(12) United States Patent
McGuckin, Jr.

(10) Patent No.: US 11,375,763 B2
(45) Date of Patent: Jul. 5, 2022

(54) HELMET WITH IMPACT TRACKING

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 86 days.

(21) Appl. No.: 16/558,007

(22) Filed: Aug. 30, 2019

(65) Prior Publication Data

US 2020/0008509 A1    Jan. 9, 2020

Related U.S. Application Data

(63) Continuation of application No. 14/604,557, filed on Jan. 23, 2015, now Pat. No. 10,413,009.

(60) Provisional application No. 61/991,463, filed on May 10, 2014, provisional application No. 61/940,407, filed on Feb. 15, 2014.

(51) Int. Cl.
*A42B 3/04* (2006.01)
*A42B 3/12* (2006.01)
*A61B 5/16* (2006.01)
*G08B 21/18* (2006.01)
*G01L 5/00* (2006.01)
*A61B 5/00* (2006.01)

(52) U.S. Cl.
CPC .............. *A42B 3/046* (2013.01); *A42B 3/128* (2013.01); *G01L 5/0052* (2013.01); *A42B 3/125* (2013.01); *A61B 5/163* (2017.08); *A61B 5/7465* (2013.01); *G08B 21/182* (2013.01)

(58) Field of Classification Search
None
See application file for complete search history.

(56) References Cited

U.S. PATENT DOCUMENTS

| | | |
|---|---|---|
| 3,713,640 A | 1/1973 | Margan |
| 4,012,794 A | 3/1977 | Nomiyama |
| 5,669,079 A | 9/1997 | Morgan |

(Continued)

FOREIGN PATENT DOCUMENTS

| | | |
|---|---|---|
| GB | 2404328 | 2/2005 |
| WO | WO 96/14768 | 5/1996 |
| WO | WO 98/19571 | 5/1998 |

OTHER PUBLICATIONS

Extended European Search Report Application No. 15153887.3 dated Jul. 15, 2015.

(Continued)

*Primary Examiner* — John C Kuan
(74) *Attorney, Agent, or Firm* — Neil D. Gershon

(57) ABSTRACT

A helmet for tracking impact including at least one sensor, a processor in communication with the sensor and a storage file in communication with the processor, the at least one sensor measures a force applied to the helmet and sends a signal to the processor indicative of the measured force. The processor receives the signal indicative of the measured force and compares the measured force to a predetermined value, wherein if the measured force exceeds the predetermined value data is sent to the storage file to record the measured force. The helmet can include an alarm system and/or an injury tracking system.

10 Claims, 17 Drawing Sheets

(56) References Cited

U.S. PATENT DOCUMENTS

| | | | |
|---|---|---|---|
| 5,950,244 A | 9/1999 | Fournier | |
| 5,978,972 A | 11/1999 | Stewart et al. | |
| 6,446,270 B1 | 9/2002 | Durr | |
| 6,720,878 B2 | 4/2004 | Jumpertz | |
| 6,798,392 B2 | 9/2004 | Hartwell et al. | |
| 6,978,162 B2 | 12/2005 | Russell et al. | |
| 7,093,305 B2 | 8/2006 | Reilly et al. | |
| 7,254,843 B2 | 8/2007 | Talluri | |
| 7,401,365 B2 | 7/2008 | Neal et al. | |
| 7,509,835 B2 | 3/2009 | Beck | |
| 7,526,389 B2 | 4/2009 | Greenwald et al. | |
| 7,570,170 B2 | 8/2009 | Wallner | |
| 8,382,685 B2 | 2/2013 | Vaccari et al. | |
| 8,537,017 B2 | 9/2013 | Mack | |
| 8,548,768 B2 * | 10/2013 | Greenwald | A61B 5/6803 600/595 |
| 8,554,495 B2 | 10/2013 | Mack | |
| 8,702,516 B2 | 4/2014 | Bentley | |
| 8,814,150 B2 | 8/2014 | Ferrara | |
| 8,860,570 B2 | 10/2014 | Thomas | |
| 8,930,144 B2 | 1/2015 | Hubler | |
| 9,451,915 B1 * | 9/2016 | Wong | A61B 5/4803 |
| 2002/0060633 A1 | 5/2002 | Crisco, III et al. | |
| 2003/0007936 A1 | 1/2003 | Robinson | |
| 2003/0140401 A1 | 7/2003 | Ku | |
| 2004/0117896 A1 | 6/2004 | Madey | |
| 2004/0250340 A1 | 12/2004 | Piper | |
| 2005/0177929 A1 | 8/2005 | Greenwald | |
| 2006/0038694 A1 | 2/2006 | Naunheim | |
| 2007/0209098 A1 | 9/2007 | Peart | |
| 2008/0256687 A1 | 10/2008 | Spencer | |
| 2010/0307223 A1 | 12/2010 | Jeftic-Stojanovski | |
| 2011/0098934 A1 | 4/2011 | Hubler | |
| 2011/0117310 A1 | 5/2011 | Anderson | |
| 2011/0181420 A1 | 7/2011 | Mack | |
| 2011/0184663 A1 | 7/2011 | Mack | |
| 2012/0096631 A1 | 4/2012 | King et al. | |
| 2012/0124720 A1 | 5/2012 | Evans et al. | |
| 2012/0198604 A1 | 8/2012 | Weber | |
| 2012/0210498 A1 | 8/2012 | Mack | |
| 2012/0223833 A1 | 9/2012 | Thomas | |
| 2012/0304367 A1 | 12/2012 | Howard et al. | |
| 2013/0013243 A1 | 1/2013 | Levine | |
| 2013/0060168 A1 | 3/2013 | Chu et al. | |
| 2013/0074248 A1 | 3/2013 | Evans et al. | |
| 2013/0110415 A1 | 5/2013 | Davis et al. | |
| 2013/0185837 A1 | 7/2013 | Phipps et al. | |
| 2013/0271602 A1 | 10/2013 | Bentley | |
| 2013/0282308 A1 | 10/2013 | Mack et al. | |
| 2014/0143940 A1 * | 5/2014 | Iuliano | A42B 3/046 2/422 |
| 2014/0173810 A1 | 6/2014 | Suddaby | |
| 2014/0345036 A1 | 11/2014 | Sargenti | |
| 2015/0040685 A1 * | 2/2015 | Nicholson | A61B 5/4064 73/862.51 |
| 2015/0109129 A1 * | 4/2015 | Merril | G08B 21/0438 340/573.1 |
| 2015/0285832 A1 | 10/2015 | Thomas | |
| 2015/0375083 A1 * | 12/2015 | Stelfox | G01S 19/48 700/91 |

OTHER PUBLICATIONS

Extended European Search Report Application No. 15153888.1 dated Jul. 13, 2015.

\* cited by examiner

HELMET WITH IMPACT TRACKING

This application is a continuation of U.S. application Ser. No. 14/604,557, filed Jan. 23, 2015, which claims the benefit of provisional application Ser. No. 61/991,463, filed May 10, 2014 and provisional application Ser. No. 61/940,407, filed Feb. 15, 2014. The entire contents of each of these applications are incorporated herein by reference.

BACKGROUND

Technical Field

This application relates to a helmet and more particularly to a helmet having built in capabilities to track impact history and/or built in capabilities to test for brain injury. The helmet can also have varying shock absorption capabilities.

Background of Related Art

Head injuries in sports are becoming more prevalent. Part of the reason for such increase in incidence of injuries is that helmets provide a false sense of security and are therefore used offensively in contact sports such as football. When two helmets crash together, full force transmission occurs, leading to concussions and more severe head injuries.

Additionally, current helmets are heavy, which adds to the discomfort. Such heaviness further adds to the false sense of security, creating a mistaken correlation between helmet weight and protection.

It would be advantageous to provide helmets with impact tracking capabilities which could further prevent injury. This would enable the storage of data relating to head impact for evaluation to assess the wearer's condition.

Additionally, current helmets are built with some shock absorption features, but such shock absorption does not vary depending on the force of impact. There exists a need for improved helmets to reduce head injuries. It would also be advantageous to provide such injury reducing capabilities without increasing the weight and/or stiffness of the helmet.

SUMMARY

The present invention overcomes the problems and disadvantages of the prior art.

In accordance with one aspect of the present invention, a helmet for tracking impact is provided comprising at least one sensor, a processor in communication with the sensor and a storage file in communication with the processor. The at least one sensor measures a force applied to the helmet and sends a signal to the processor indicative of the measured force, the processor receiving the signal indicative of the measured force and compares the measured force to a predetermined value, wherein if the measured force exceeds the predetermined value data is sent to the storage file to record the measured force.

In some embodiments, if the measured force does not exceed the predetermined value, it is considered a non-event and data is not sent from the processor to the storage file.

In some embodiments, the data sent to the storage file includes one or more of a type of injury, a location of injury and a time of injury. The measured force can be a rotational force applied to a head of a wearer of the helmet and/or an impact force applied to the head of the wearer and the data can include a force value of the measured force. In some embodiments, the storage file updates a register to include the data in the register. In some embodiments, the register is repeatedly updated as additional data is received in response to subsequent measured forces detected which exceed a predetermined value, the data being retrievable for evaluation.

The helmet, in some embodiments, includes a plurality of shock absorbers including at least one first shock absorber having a first shock absorption characteristic and at least one second shock absorber having a second shock absorption characteristic, the second shock absorption characteristic being different than the first shock absorption characteristic wherein the first shock absorption characteristic provides a lower activation threshold than the second shock absorption characteristic such that activation of the first and second sets of shock absorbers is dependent on the force impact to the helmet.

In accordance with another aspect of the present invention a helmet for tracking impact is provided comprising at least one sensor, a processor in communication with the sensor, a storage file in communication with the processor, and an alarm system in communication with the processor. The at least one sensor measures a force applied to the helmet and sends a first signal to the processor indicative of the measured force. The processor receives the first signal indicative of the measured force and compares the measured force to a predetermined value, wherein if the measured force exceeds the predetermined value a second signal is sent to the alarm system to activate an alarm.

In some embodiments, if the impact force does not exceed the predetermined value data is sent to the storage file containing details of the force applied to the helmet.

In some embodiments, the data sent to the storage file includes one or more of a type of injury, a location of injury, and a time of injury. The measured force can be a rotational force and/or an impact force applied to a head of a wearer of the helmet and the data can include a force value of the measured force. In some embodiments, the storage file updates a register and the data is stored in the register. In some embodiments, the register is repeatedly updated as additional data is received in response to subsequent measured forces detected which exceed a predetermined value, the data being retrievable for evaluation.

In some embodiments, the measured force is initially compared by the processor to a threshold value less than the predetermined value, and if the measured force is less than the threshold value it is computed as a non-event and no data is sent to the storage file by the processor.

In some embodiments, if the alarm is activated, data is sent to the storage file indicative of one or more of a type of injury, a location of injury, and a time of injury.

The helmet can include an algorithm in the processor which computes cumulative values indicative of impact history and the cumulative values are compared to threshold values, and if the cumulative values exceed the threshold values, a third signal is sent to the alarm to trigger the alarm.

In some embodiments, the helmet includes an outer shell having an inner surface and an outer surface and a plurality of shock absorbers, the shock absorbers being positioned internal of the outer shell and including at least one first shock absorber having a first shock absorption characteristic and at least one second shock absorber having a second shock absorption characteristic, wherein the second shock absorption characteristic is different than the first shock absorption characteristic and the first shock absorption characteristic provides a lower activation threshold than the second shock absorption characteristic such that activation of the first and second sets of shock absorbers is dependent on the force impact to the helmet.

In accordance with another aspect of the present invention, a helmet for tracking impact is provided comprising an alarm system, at least one sensor, a processor in communication with the sensor, a storage file in communication with the processor, and an injury tracking system in communication with the processor. The at least one sensor measures a force applied to the helmet and sends a first signal to the processor indicative of the measured force. The processor receives the first signal indicative of the measured force and compares the measured force to a predetermined value, wherein if the measured force exceeds the predetermined value a second signal is sent to the injury tracking system to activate the injury tracking system.

In some embodiments, if the measured force does not exceed the predetermined value, it is considered a non-event and the injury tracking system is not activated.

In some embodiments, the impact tracking system includes a transmitter to transmit commands to a wearer of the helmet and responses of the wearer are inputted to and evaluated by a processor. The commands can be visual instructions to be followed by the wearer and/or audio instructions to be followed by the wearer. The impact tracking system can include a data display to display the commands to the wearer. The display can be provided on a face cover of the helmet.

In some embodiments, if input of the wearer does not fall within a preset set of parameters, a signal is sent by a processor to the alarm system to trigger an alarm and if input of the wearer to the processor satisfies the set of parameters, a signal is not sent to the alarm system and the injury tracking system is reset for later activation if necessary.

The helmet preferably includes a power supply mounted therein.

In some embodiments, the measured force is initially compared by the processor to a threshold value less than the predetermined value, and if the measured force is less than the threshold value it is computed as a non-event and no data is sent to the storage file by the processor. In some embodiments, if the measured force does not exceed the predetermined value, data is sent to the storage file containing details of the force applied to the helmet. The data sent to the storage file can include one or more of a type of injury, a location of injury, and a time of injury. The measured force can be a rotational force and/or an impact force applied to a head of a wearer of the helmet and the data can include a force value of the measured force.

In some embodiments, the storage file updates a register and the data is stored in the register. In some embodiments, the register is repeatedly updated as additional data is received in response to subsequent measured forces detected which exceed a predetermined value, the data being retrievable for evaluation.

An algorithm can be provided in the processor which computes cumulative values indicative of impact history and the cumulative values are compared to threshold values, and if the cumulative values exceed the threshold values, a third signal is sent to the alarm to trigger the alarm.

In some embodiments, the helmet includes an outer shell having an inner surface and an outer surface and a plurality of shock absorbers, the shock absorbers being positioned internal of the outer shell and including at least one first shock absorber having a first shock absorption characteristic and at least one second shock absorber having a second shock absorption characteristic, wherein the second shock absorption characteristic is different than the first shock absorption characteristic and the first shock absorption characteristic provides a lower activation threshold than the second shock absorption characteristic such that activation of the first and second sets of shock absorbers is dependent on the force impact to the helmet.

The helmets described above can in some embodiments include varying shock absorption. In some embodiments, the shock absorbers are composed of a compressible foam material. In some embodiments, the shock absorbers comprise air cells forming an air pocket. The air cells can include a relief valve to allow force deceleration and pressure release when a pressure threshold is exceeded. In some embodiments, the shock absorbers of a first set have a first height and the shock absorbers of the second set have a second height, the first height being greater than the second height.

The foregoing helmets can have an outer shell that spins or rotates with respect to the helmet body to release energy to a side. The outer shell can have a low friction outer surface to deflect impact to the helmet.

The foregoing helmets can include a third set of shock absorbers having a gradient of stress absorption different than the gradient of the first set of shock absorbers and the gradient of the second set of shock absorbers thereby providing successive loading based on severity of force impact to the helmet.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
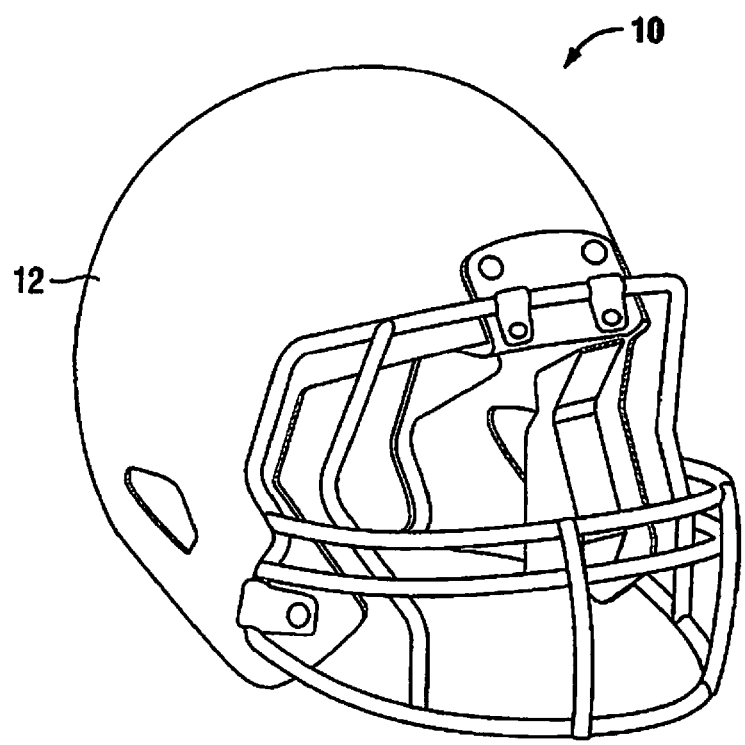
FIG. 1 is a perspective view of a helmet of the prior art having a hard outer shell and soft inner padding.

FIG. 1 illustrates a football helmet of the prior art. The helmet 10 has a hard outer shell 12 and soft padding inside the shell 12. The helmet 10 is relatively heavy and relies on the soft padding inside to cushion the head in an attempt to reduce brain injuries. However, the weight of the helmet makes the helmet cumbersome and uncomfortable to wear. The heavy weight can also adversely affect athletic performance.

Additionally, the padding inside the helmet does not provide adequate protection to the head, especially since the heavy helmet provides the wearer with a false sense of protection. This false sense of protection oftentimes lead to more head injuries since the helmet is used offensively as the wearer uses the helmet as a direct force against an opponent, and the wearer will incur direct impacts on the helmet.

Moreover, the amount of padding that can be provided in the helmet of the prior art is limited by the size of the helmet since if thicker padding is utilized it will take up more internal space, leading to even larger and more cumbersome helmet. Additionally, if such additional padding/cushioning is added, it would need to be sufficient to handle all impacts, regardless of the force. Therefore, the helmet would need to be designed with thicker cushioning throughout, even if not necessary to handle small impact forces. Also, if the helmet is designed solely to accommodate maximum impact, it will be stiffer and "bumpier" on the user's head.

Helmets with varying Shock Absorption

The present invention advantageously in some aspects provides a lightweight helmet without sacrificing effectiveness in injury prevention. This is achieved through the varying shock absorbers (shock absorbing members) lining the helmet. Additionally, the helmet is designed in certain embodiments so that upon certain impact forces, the outer shell spins with respect to the helmet body, thus further dispersing the force of the impact.

Figure 2A:
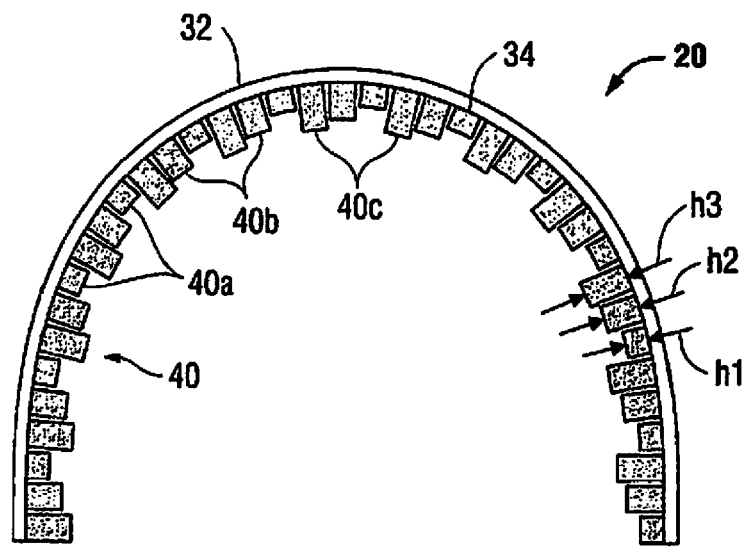
FIG. 2A is a front view of a first embodiment of the inner (inside) liner of the helmet of a first embodiment of the present invention.
Figure 2B:
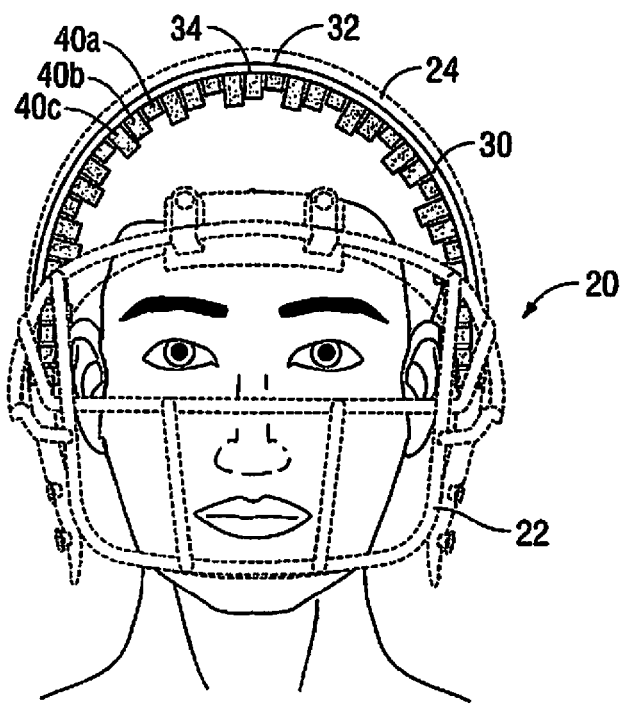
FIG. 2B is an enlarged front view of the helmet of the first embodiment of the present invention with portions removed to show the inner liner of FIG. 2A.
Figure 3:
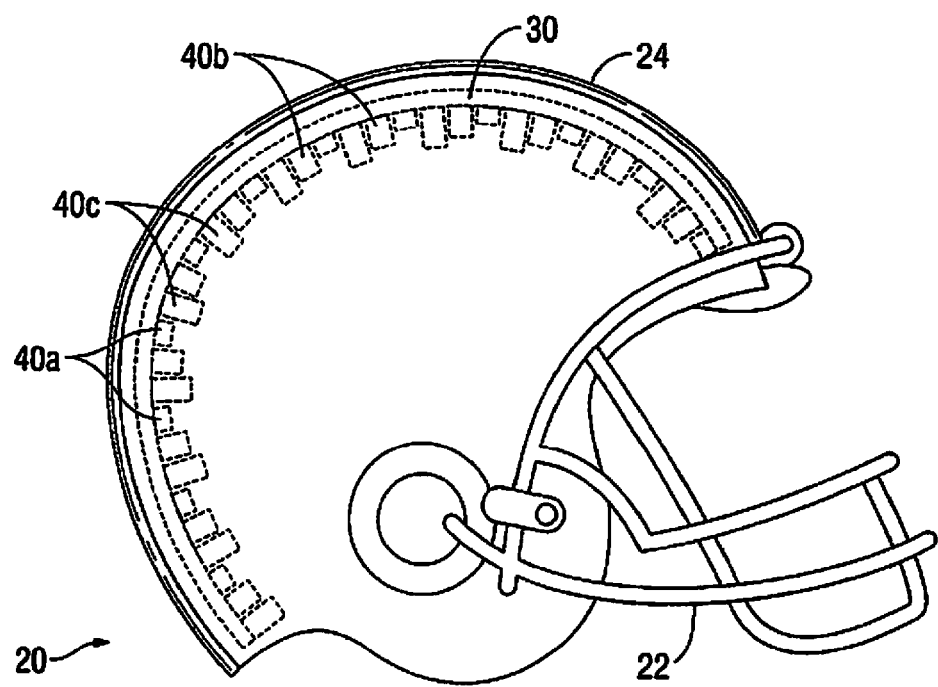
FIG. 3 is a side view of the helmet of FIG. 2B.

Turning now to the drawings, wherein like reference numerals identify similar or like components throughout the several views, FIGS. 2A-3 illustrate a first embodiment of the helmet of the present invention. The helmet is designated generally by reference number 20 and has a conventional face guard 22. Inside the outer shell 24 of the helmet 20 is an inner liner 30 which forms the shock absorbing feature of the present invention. Inner liner 30 has an upper surface 32 which is attached to the inner surface of the outer shell 24 and a lower surface 34 from which the shock absorbers 40 extend.

Shock absorbers in the embodiment of FIGS. 2A-3 are composed of a compressible foam material with sufficient flexibility and rigidity to receive and disperse a force applied thereto. The shock absorbers 40 are of varying height and of varying compressibility thereby providing different shock absorbing characteristics with different activation thresholds. In the embodiment of FIGS. 2A-3, there are three sized shock absorbers with shock absorbers 40a of the smallest height h1 having a first shock absorption characteristic, shock absorbers 40c of the largest height h3 having a second shock absorption characteristic and shock absorbers 40b of an intermediate height h2 having a third shock absorption characteristic. Height h2 is greater than height h1 and less than height h3. The shock absorbers 40a, 40b and 40c are collectively referred to as shock absorbers 40. For clarity, only some of the shock absorbers 40a, 40b and 40c are labeled throughout the drawings. It can be appreciated that shock absorbers of more than three differing heights can be provided. It is also contemplated that shock absorbers of only two different heights can be provided. In any event, the liner will have at least one, and preferably a first set of shock absorbers, having a first shock absorption characteristic, and at least another shock absorber, and preferably a second set of shock absorbers, having a second shock absorption characteristic different than the first shock absorption characteristic. Also, the shock absorbers 40 can be arranged in a pattern or grouping different than that the alternating pattern shown in FIGS. 2A-3. As noted above, shock absorbers 40 can be formed of a compressible foam material which compresses upon sufficient impact. However, other cushioning materials are also contemplated.

Figure 5A:
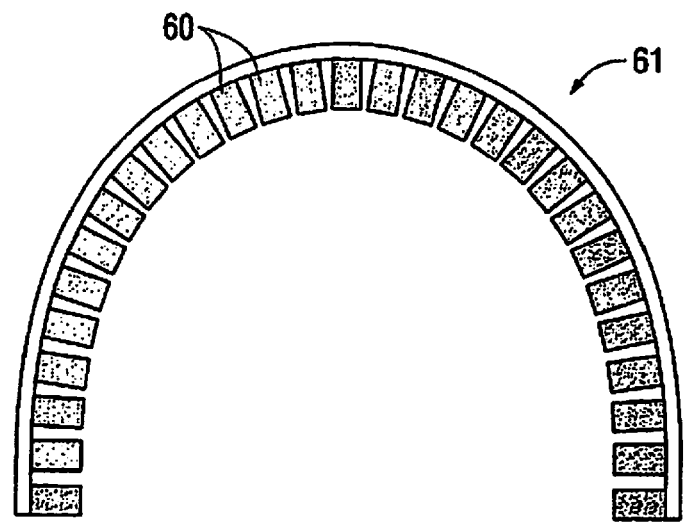
FIG. 5A is a front view of an alternate embodiment of the inner liner of the helmet of the present invention having equally sized shock absorbers.
Figure 5B:
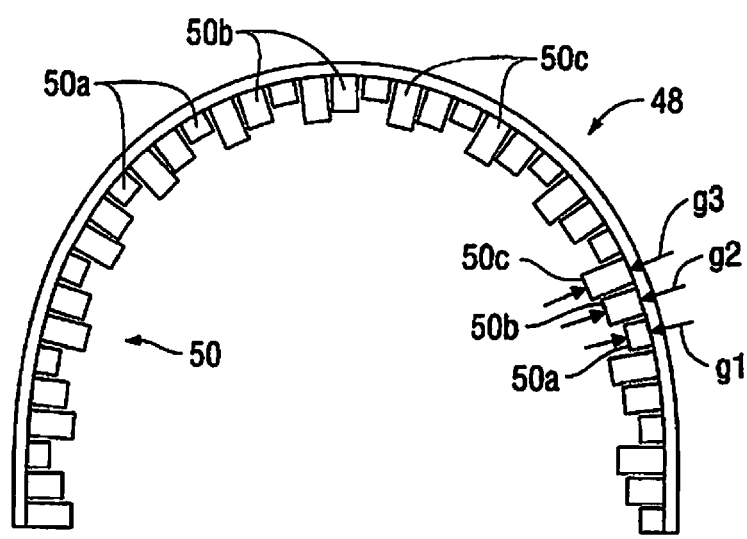
FIG. 5B is a front view of another alternate embodiment of the inner liner of the helmet of the present invention having shock absorbers of varying heights.

In the alternate embodiment of FIG. 5B, the shock absorbers 50 of inner liner 48 include shock absorbers 50a of the smallest height g1, shock absorbers 50c of the largest height g3 and shock absorbers 50b of an intermediate height g2 which is greater than height g1 and less than height g3. The shock absorbers 50a, 50b and 50c are collectively referred to as shock absorbers 50. For clarity only some of the shock absorbers 50a, 50b, and 50c are labeled in FIG. 5B. In this embodiment, the shock absorbers comprise air cells rather than a foam material as in FIG. 2A, and the air cells can include a relief valve. In all other respects the shock absorbing feature of FIG. 5A is identical to that of FIG. 2A and is used in a similar helmet as that shown in FIG. 2B. As can be appreciated, as explained above with respect to the embodiment of FIG. 2A, although three sets of varying shock absorbers arranged in an alternating pattern are shown, a different number of sets of varying shock absorbers and/or a different pattern is contemplated.

Figure 6:
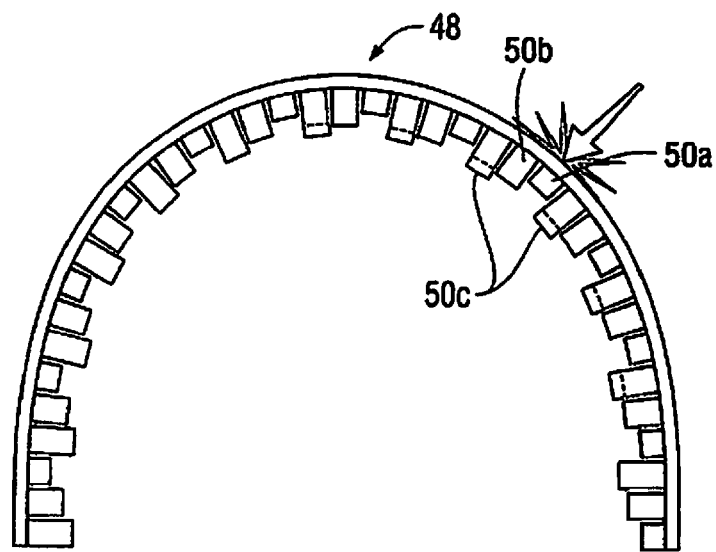
FIG. 6 is a front view of the inner liner of FIG. 5B showing the effect upon a small impact force on the helmet.
Figure 7:
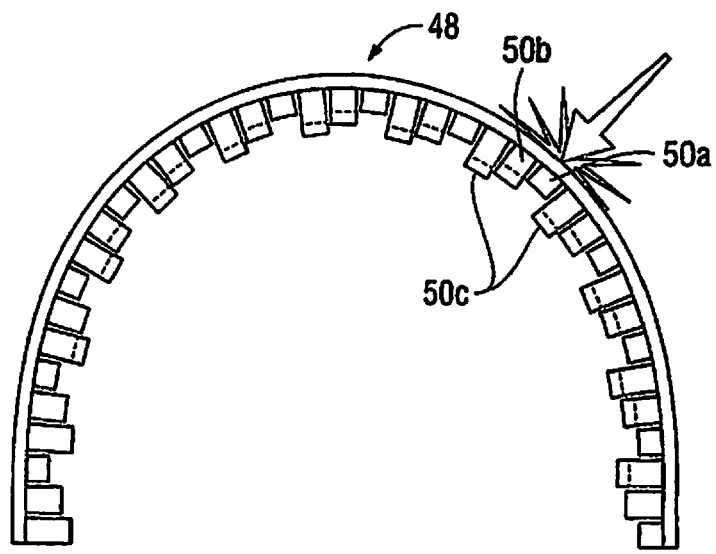
FIG. 7 is a front view of the inner liner of FIG. 5B showing the effect upon a medium impact force on the helmet.
Figure 8:
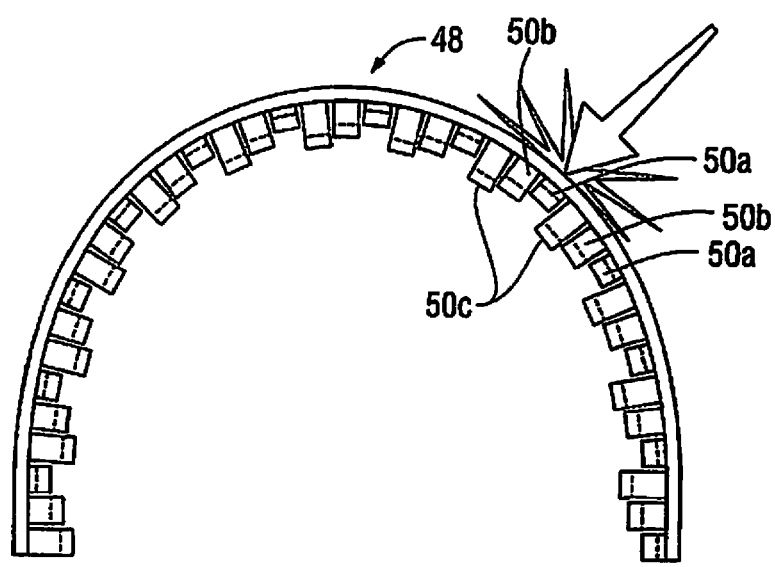
FIG. 8 is a front view of the inner liner of FIG. 5B showing the effect upon a large impact force on the helmet.

FIGS. 6-8 illustrate what occurs upon impact of varying forces on the helmet. Although FIGS. 6-8 illustrate the inner liner 48 of FIG. 5B, the inner liner 30 of FIG. 2A would function and react in the same manner as shown in FIGS. 6-8. The shock absorbers 50 (like shock absorbers 40) of varying heights have different gradients of stress absorption and therefore different thresholds for activation and provide successive loading dependent on severity of force impact. Consequently, if a relatively small impact force is applied to the helmet as shown in FIG. 6, only a few of the shock absorbers would be activated, i.e., shock absorbers 50c which have the most flexibility and lowest activation threshold. If a greater impact is applied to the helmet as in FIG. 7, both the larger shock absorbers 50c and the intermediate shock absorbers 50b would be affected and activated. If an even larger impact is applied as in FIG. 8, smaller shock absorbers 50a would also be impacted as shock absorbers 50a have the smallest height, least flexibility and highest activation threshold. That is, all sized absorbers 50 would be activated to absorb and disperse the force. In this manner, only those shock absorbers necessary to absorb the shock would be activated, allowing for a series of smaller shock absorbers, taking up less room in the helmet and also reducing the weight of the helmet than would otherwise be necessary. Note shock absorbers 40 would be activated in the same manner as shock absorbers 50, i.e., dependent on impact force.

It should be appreciated that in FIGS. 6-8, multiple or all of the shock absorbers 50 are shown impacted, however depending on the impact, only certain shock absorbers 50a, 50b, and 50c would be affected. For example, in certain instances, only the shock absorbers in the region of impact would be affected/activated. On sufficient impact, it is also possible that all shock absorbers of the liner 48 would be affected/activated. This is also applicable to liner 30 and shock absorbers 40 as well as the other shock absorbers disclosed herein, e.g., shock absorbers 60 and 70 described below.

In the embodiment of FIG. 5A, the shock absorbers 60 of inner liner 61 are of the same height but varying shock absorption is achieved by providing different materials. The embodiment of FIG. 5A can have the same advantages of reduced bulk as in the previously described embodiments achieved by varying the lightness of the material. It also has the advantage of varying shock absorption, wherein only a fraction of the shock absorbing elements are activated upon application of a relatively low force, i.e., the shock absorbers with the greatest flexibility/compressibility, and more shock absorbers are activated with application of a higher force i.e., including the shock absorbers having less flexibility/compressibility. Such varying shock absorption can be achieved using a pattern similar to that of the embodiments of FIGS. 2A and 5B, e.g., three sets of shock absorbers of different shock absorption characteristics arranged in an alternating pattern with a first set of first flexibility/compressibility, a second set of a different, e.g., less flexibility/compressibility and a third set of a still different, e.g., even less flexibility/compressibility. It should be appreciated that as in the aforedescribed embodiments, a different number of sets of varying shock absorbers and/or different patterns of the varying shock absorbers are also contemplated.

In some embodiments, the shock absorbers of the various embodiments described herein can contain material such as foam. Alternatively the shock absorbers can contain a fluid with a relief valve for releasing pressure when the pressure is greater than a pressure threshold to reduce the effects of impact to the head. The relief valves allow for force deceleration and would have different thresholds for release to provide shock absorbers of varying shock absorption characteristics. In other embodiments, some of the shock absorbers can contain compressible surfaces such as foam and other shock absorbers can contain fluid with a relief valve.

Thus, the shock absorbers in accordance with the present disclosure can have different configurations, different heights and/or different materials to accommodate different forces, thus providing differential protection. They can be arranged in an alternating arrangement or grouped together in a different pattern. They can be arranged in two or more sets of varying shock absorption characteristics and can be evenly or unevenly distributed. The number of shock absorbers for each set can be the same or alternately a different number in each set.

Figure 9:
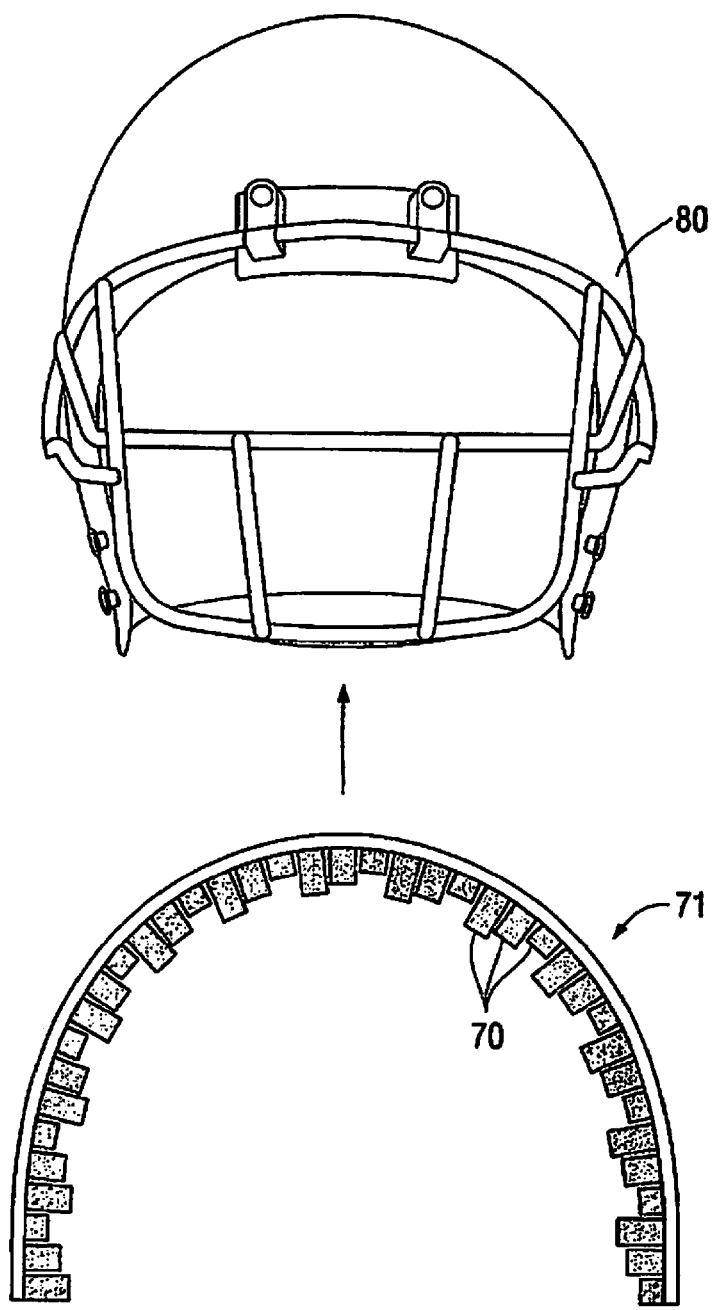
FIG. 9 is a front view of an alternate embodiment of the helmet of the present invention having an inner liner insertable into a helmet.

The inner liner with the aforedescribed shock absorbing features can be provided as a non-removable component attached to the helmet e.g., helmet 20. Alternatively, as shown in the embodiment of FIG. 9, the inner liner 71 with shock absorbers 70 can be a separate component insertable into a conventional helmet 80 and attached thereto by various methods such as adhesive or clips or other methods. The liner 71 shown in FIG. 9 has the shock absorbers of FIG. 2A but other liners with other shock absorbers described herein e.g., shock absorbers 50 or 60 could also be provided as attachable and/or removable inner liners.

Figure 4C:
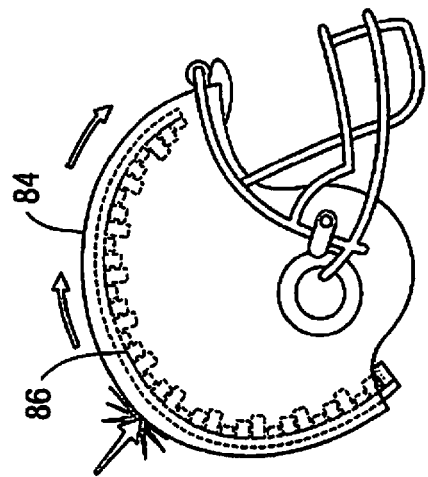
FIG. 4C is a side view illustrating rotation of the outer body of FIG. 4A upon impact at a rear region of the helmet.
Figure 4B:
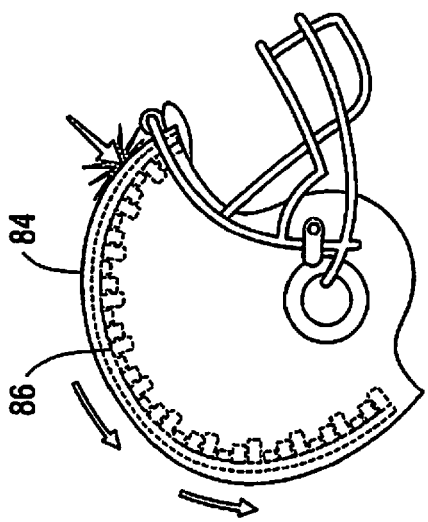
FIG. 4B is a side view illustrating rotation of the outer body of FIG. 4A upon impact at a front region of the helmet.
Figure 4A:
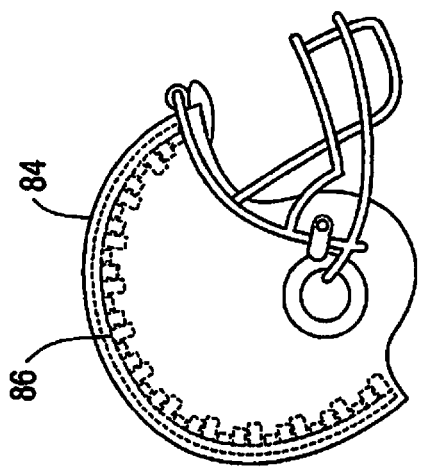
FIG. 4A is a side view of an alternate embodiment of the helmet of the present invention having a rotatable outer body, the helmet shown prior to impact.

The outer shell of the helmet of the present invention in some embodiments can be rotatable with respect to the helmet body. This helps to deflect the force to minimize direct hit impact. This is shown for example in FIGS. 4B and 4C, represented by the directional arrow showing for example a front impact causing rotation of the outer body 84 with respect to the inner liner 86 and FIG. 4C illustrating rotation of the outer body 84 upon a rear impact force. The outer shells of the helmets of the other embodiments disclosed herein (with associated shock absorbers) can likewise in some embodiments be rotatably mounted to the helmet body so they can rotate as in FIGS. 4B and 4C.

In some embodiments, any of the aforedescribed helmets can have a low friction outer surface, and even an enhanced slippery outer surface, by providing a low friction coating or low friction outer layer to aid in a glancing or deflecting rather than a direct hit. That is, the lower friction outer surface deflects the force to the helmet.

Figure 10A:
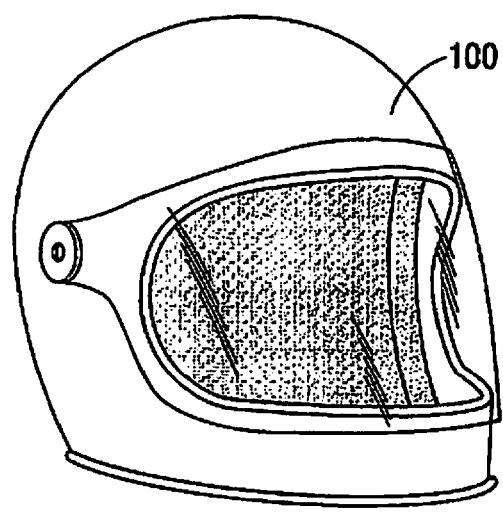
FIG. 10A is a perspective view of a motorcycle helmet having an inner liner of the present invention.
Figure 10B:
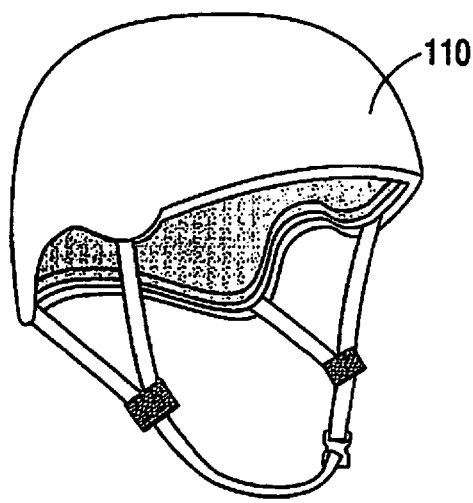
FIG. 10B is a perspective view of a bicycle helmet having an inner liner of the present invention.
Figure 10C:
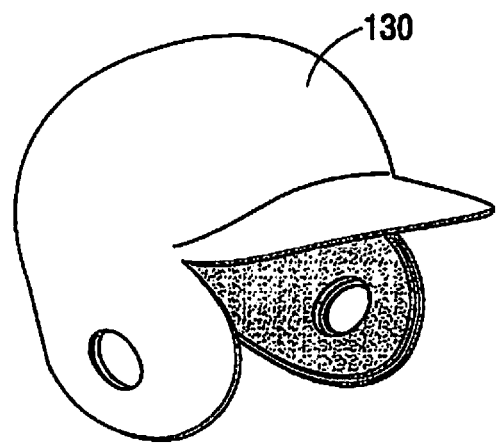
FIG. 10C is a perspective view of a baseball helmet having an inner liner of the present invention.

Helmets for other sports and uses are also contemplated. FIGS. 10A-10C show examples of different helmets which can contain any of the inner liners and shock absorbers of the present invention described herein, either permanently attached or as an attachable (mountable) insert as in FIG. 9. FIG. 10A illustrates a motorcycle helmet 100, FIG. 10B illustrates a bicycle helmet 110 and FIG. 10C illustrates a baseball batter's helmet 130. Other helmets are also contemplated including for example helmets for lacrosse, field hockey, etc.

Helmets with Impact Tracking

Figure 14A:
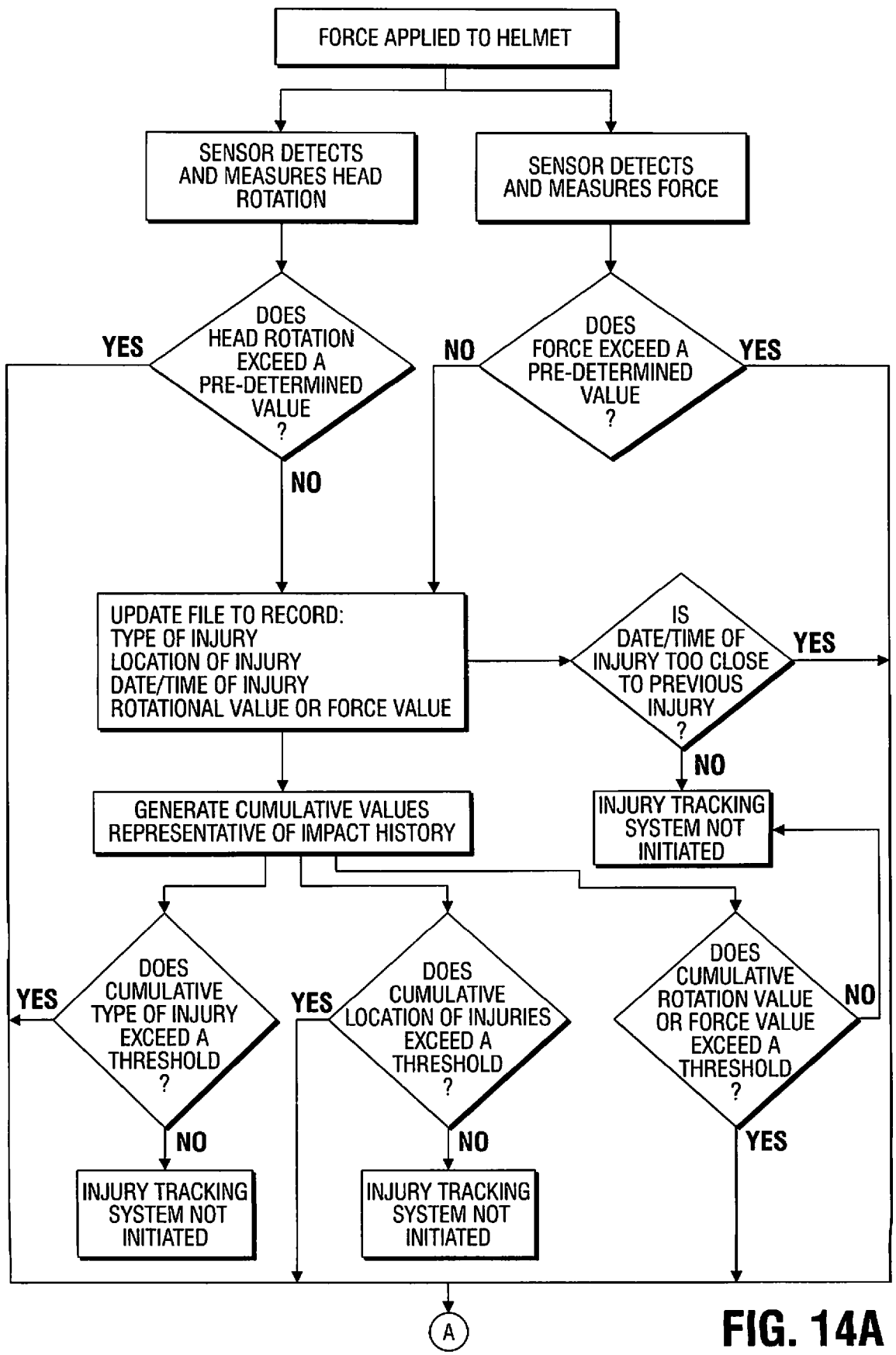
FIG. 14A, 14B is a flow chart showing a fourth embodiment of an impact tracking helmet of the present invention wherein an injury tracking system is triggered/activated if the rotational movement or direct impact, either upon initial measurement or upon cumulative calculation, exceeds a predetermined value.
Figure 14B:
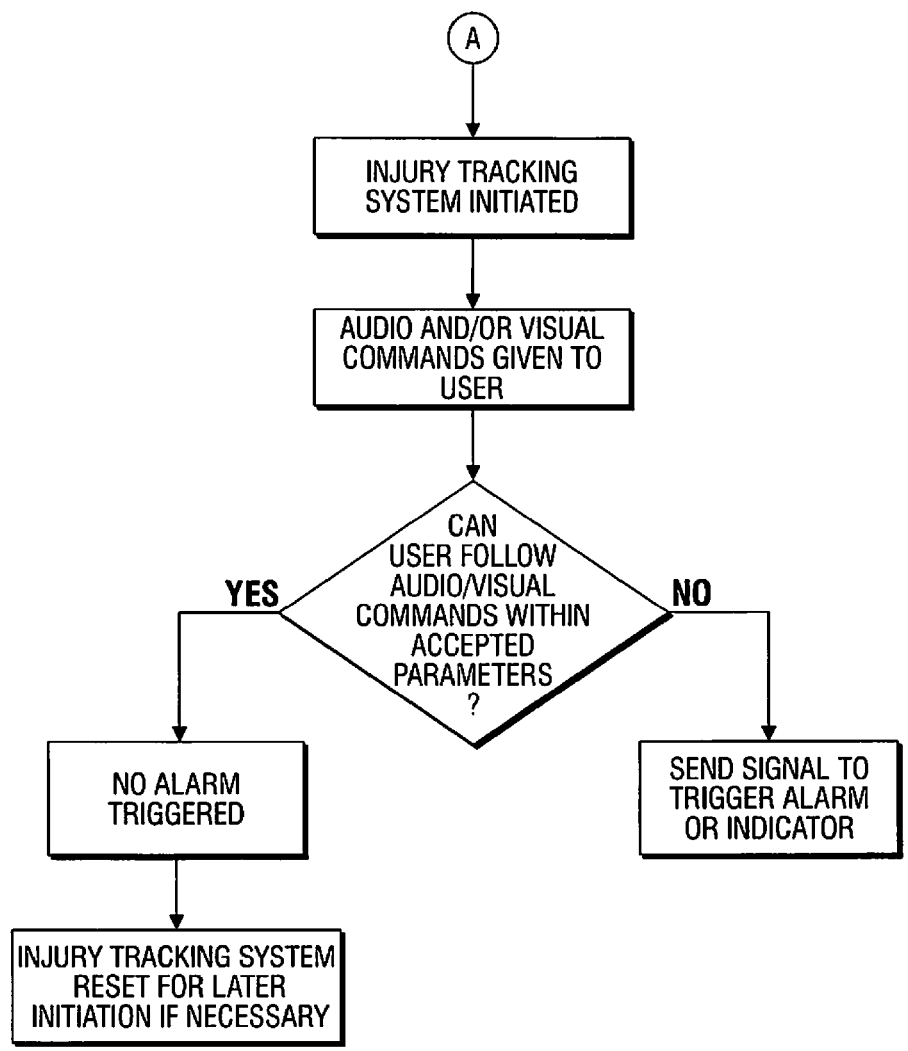
Figure 15:
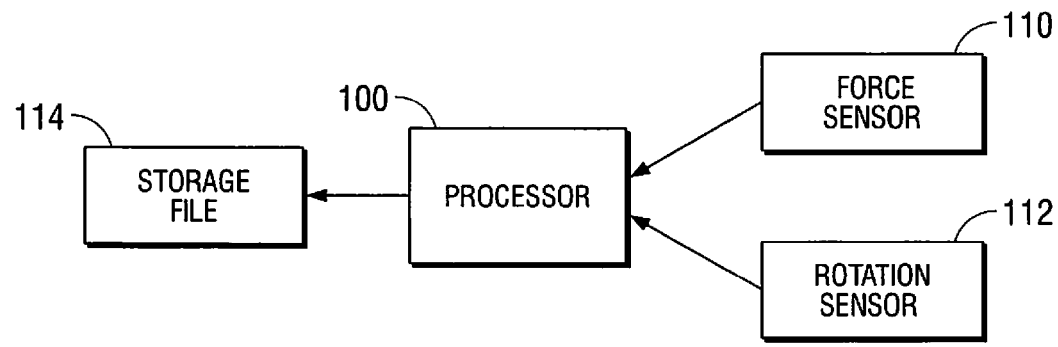
FIG. 15 is a schematic block diagram showing the system of FIG. 11.
Figure 16:
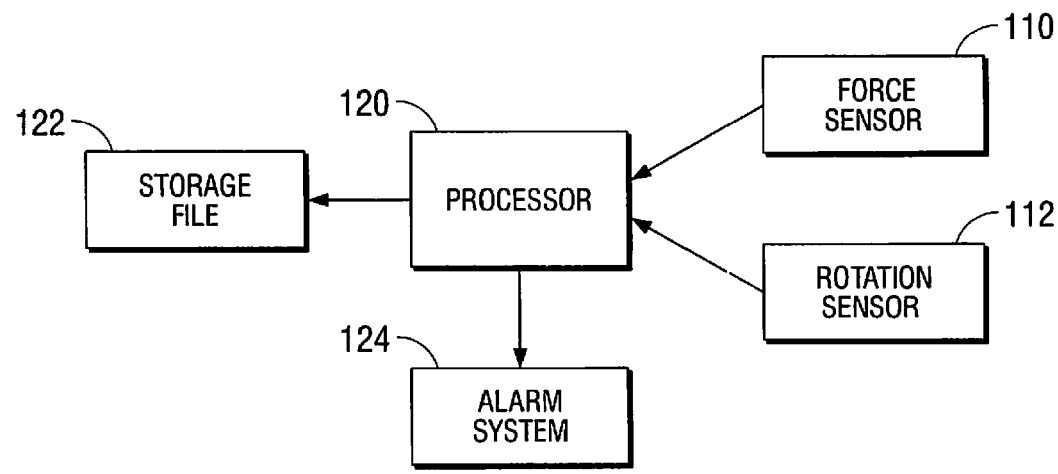
FIG. 16 is a schematic block diagram showing the system of FIG. 12.
Figure 17:
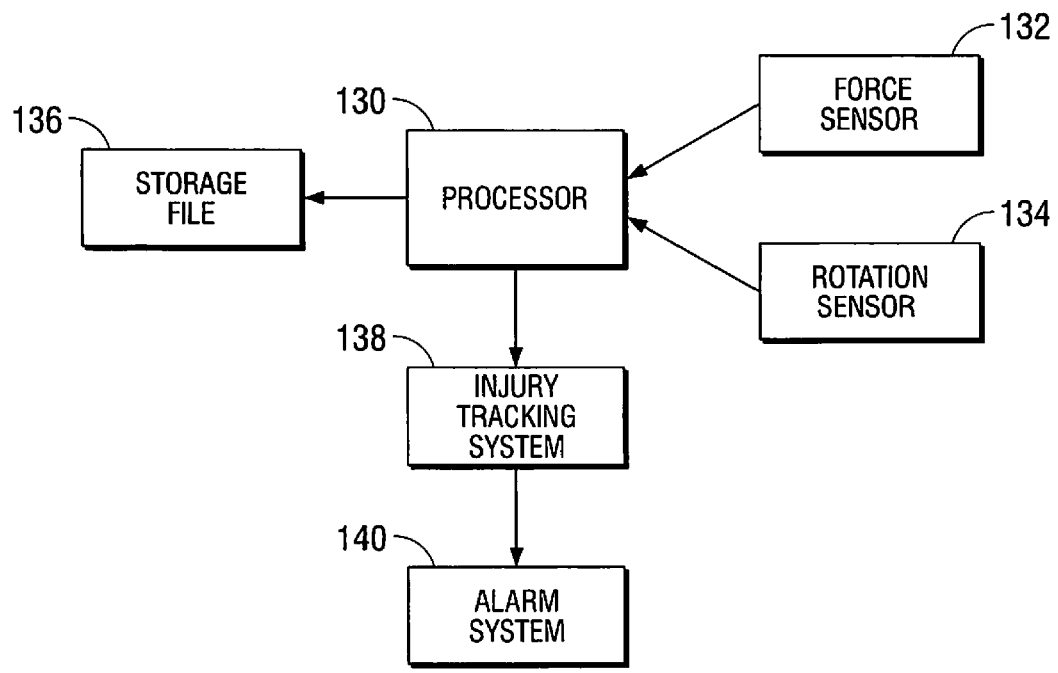
FIG. 17 is a schematic block diagram showing the system of FIG. 13.

FIGS. 11-14 illustrate flow charts of various embodiments of helmets of the present invention having impact tracking capabilities and FIGS. 15-17 are schematic block diagrams of the systems of FIGS. 11-14. The helmets of these embodiments can be used in combination with the helmets of varying shock absorption features of FIGS. 1-10 described above or alternatively can be used with helmets without the varying shock absorption features described above. In either case, the helmets as disclosed in FIGS. 11-18 track and store impact history of the wearer to thereby prevent further injury to the wearer.

Figure 18:
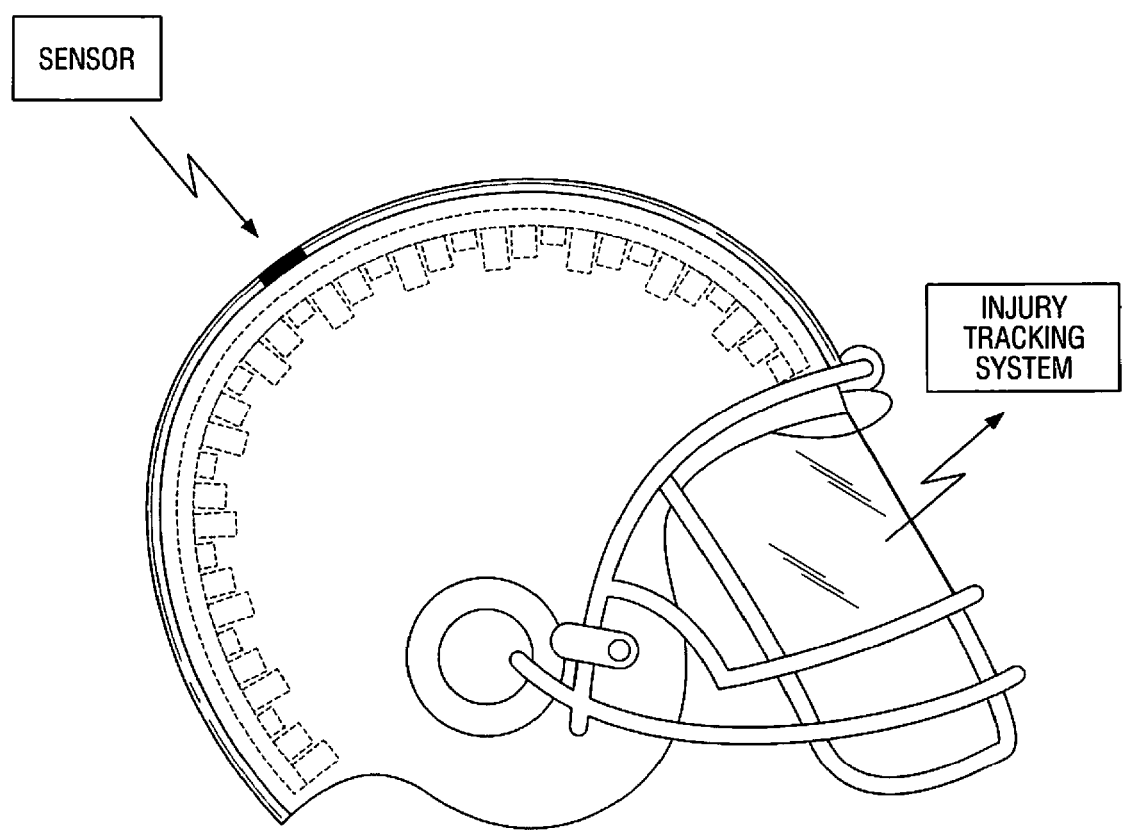
FIG. 18 is perspective view of an embodiment of the helmet having a tracking system and display screen.

FIG. 18 illustrates by way of example a helmet containing a sensor for measuring impact and an injury tracking system discussed in detail below. FIG. 18 also illustrates three sets of shock absorbers corresponding to the shock absorbers of FIG. 5B to provide varying shock absorbing characteristics as described above. The other aforedescribed shock absorbers can also be utilized. However, in alternate embodiments, such shock absorbers of FIGS. 1-10 would not be utilized and conventional shock absorption would be utilized in the helmets of FIGS. 11-18. Note the various types of helmets of FIGS. 10A-10C, with or without the aforedescribed shock absorbers, as well as helmets for other uses, can also contain the sensors, storage file and impact tracking of the present invention.

Figure 11:
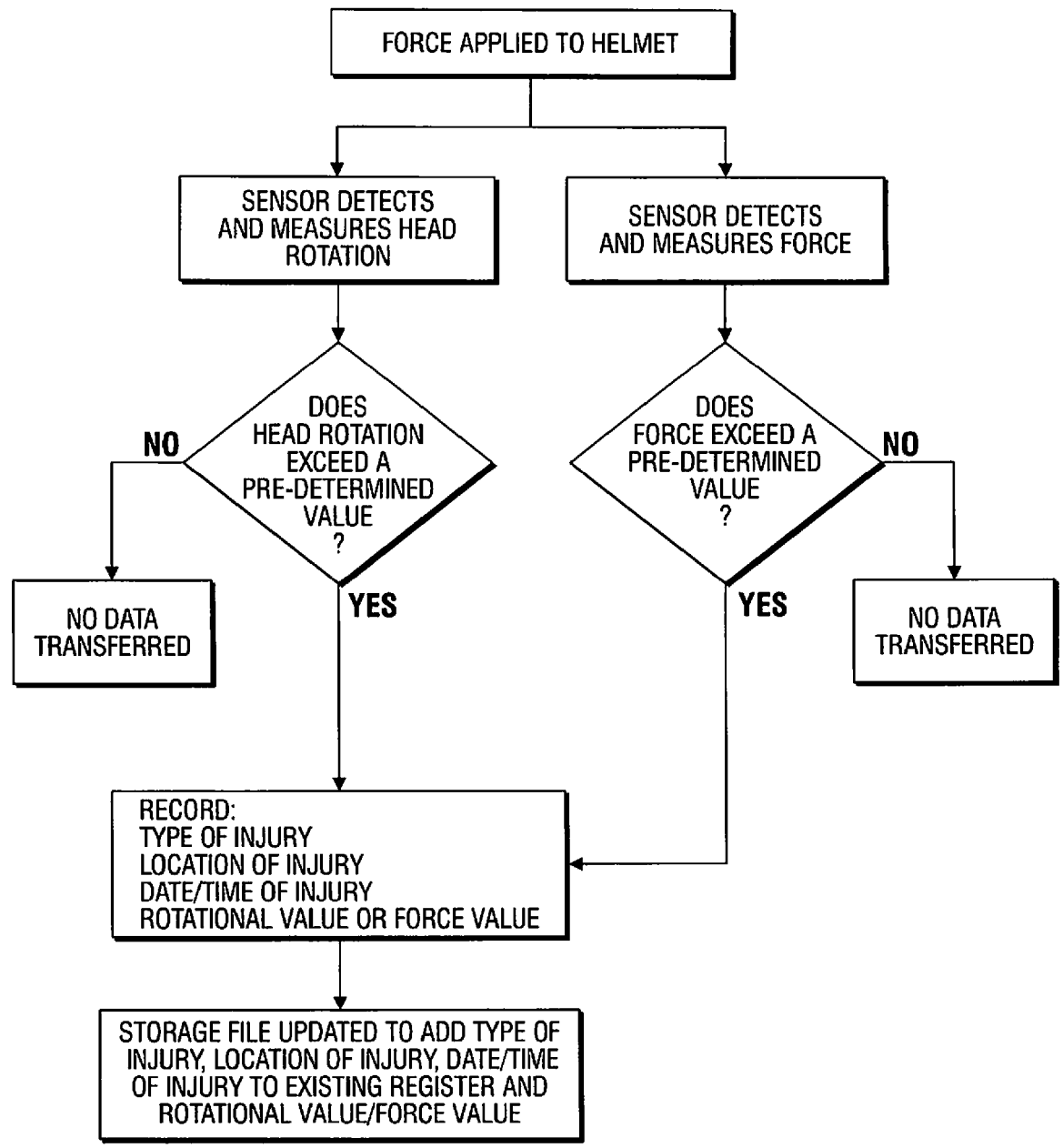
FIG. 11 is a flow chart showing a first embodiment of an impact tracking helmet of the present invention wherein rotational movement and direct impact to the helmet/head is measured and stored within the helmet to provide a history of impact.

Turning to a first embodiment of the impact tracking helmet of the present invention, the system provided in the helmet is illustrated in the schematic block diagram of FIG. 15 and in the flow chart of FIG. 11. In this embodiment, the helmet wearer's history is tracked and stored within the helmet. That is, information relating to helmet impact can be tied to the player's career and tag coded to the individual. As shown in the flow chart, when a force is applied to the helmet, which can be in the form of an external impact, e.g., a direct blow to the head, or in the form of a rotational force, e.g., a jerking motion to the head, a sensor(s) within the helmet detects and measures such force. One or more sensors can be provided and located in various locations in or on the helmet.

If head rotation is detected by the sensor 112 (FIG. 15), the sensor 112 sends a signal to the processor 100 indicative of the measured rotational force. The processor 100 receives the signal indicative of the measured rotational force R2 where it is compared to a predetermined or threshold value R1. If the rotational force value R2 does not exceed such predetermined value R1, then it is determined (computed) a "non-event" and no data is transferred by the processor 100 to the storage file 114. This ensures that minor movements of the head which have no actual or cumulative effect on the wearer are not added to the storage file (memory) and skew future comparative analysis.

If, however, the measured force value R2 exceeds the predetermined value R1, then it constitutes an injury incident and the data is sent to the storage file 114 to record one or more, and preferably all, of the following data: a) the type of injury; 2) the exact location of the injury; 3) the date and time of injury; and 4) the force value. After this information is recorded, the storage file is updated to add this information, i.e., type, location, date/time of injury and force, to the existing register so a cumulative record can be maintained, thereby tracking the wearer's history. For example, by recording the location of the injury (or impact), it can be determined if the user has received repeated injury (or impact) to the same region of the head which alone might not be serious but from a cumulative standpoint can be significant and troublesome. Similarly, if the injury has occurred in a shortened period of time, this presents a greater risk to the wearer than if over a more extended period of time. Also, the total value over multiple impact forces could translate to a significant risk. Thus, the storage file updates a register to include the data in the register. The register is repeatedly updated as additional data is received in response to subsequent measured forces exceeding the predetermined value. The register enables that at any given time, the player's injury history can be retrieved from memory, and reviewed and evaluated and necessary steps can be taken to prevent further injury.

With continued reference to the system and method of FIGS. 11 and 15, if an external force (impact) F2 is detected by the sensor 110, the sensor 110 sends a signal to the processor 100 indicative of the measured impact force F2. The processor 100 receives the signal indicative of the measured force F2 where it is compared to a predetermined or threshold force value F1. If the force F2 does not exceed such predetermined value F1, then it is determined (computed) a "non-event" and no data is transferred to the storage file 114. This ensures that minor impact to the head which have no actual or cumulative effect on the wearer are not added to memory and skew future comparative analysis.

If, however, the measured force value F2 exceeds the predetermined value F1, then it constitutes an injury incident and the data is transferred to the storage file to record one or more, and preferably all, of the following data: a) the type of injury; 2) the exact location of the injury; 3) the date and time of injury; and 4) the force value. After this information is recorded, the storage file 114 is updated to add this information, i.e., type, location, date/time of injury and force, to the existing register so a cumulative record can be maintained. Such recordation and storage has the advantages identified above with evaluation of rotational force R2. In this manner, at any given time, the player's injury history can be retrieved from memory, reviewed and evaluated and necessary steps can be taken to prevent further injury.

Figure 12:
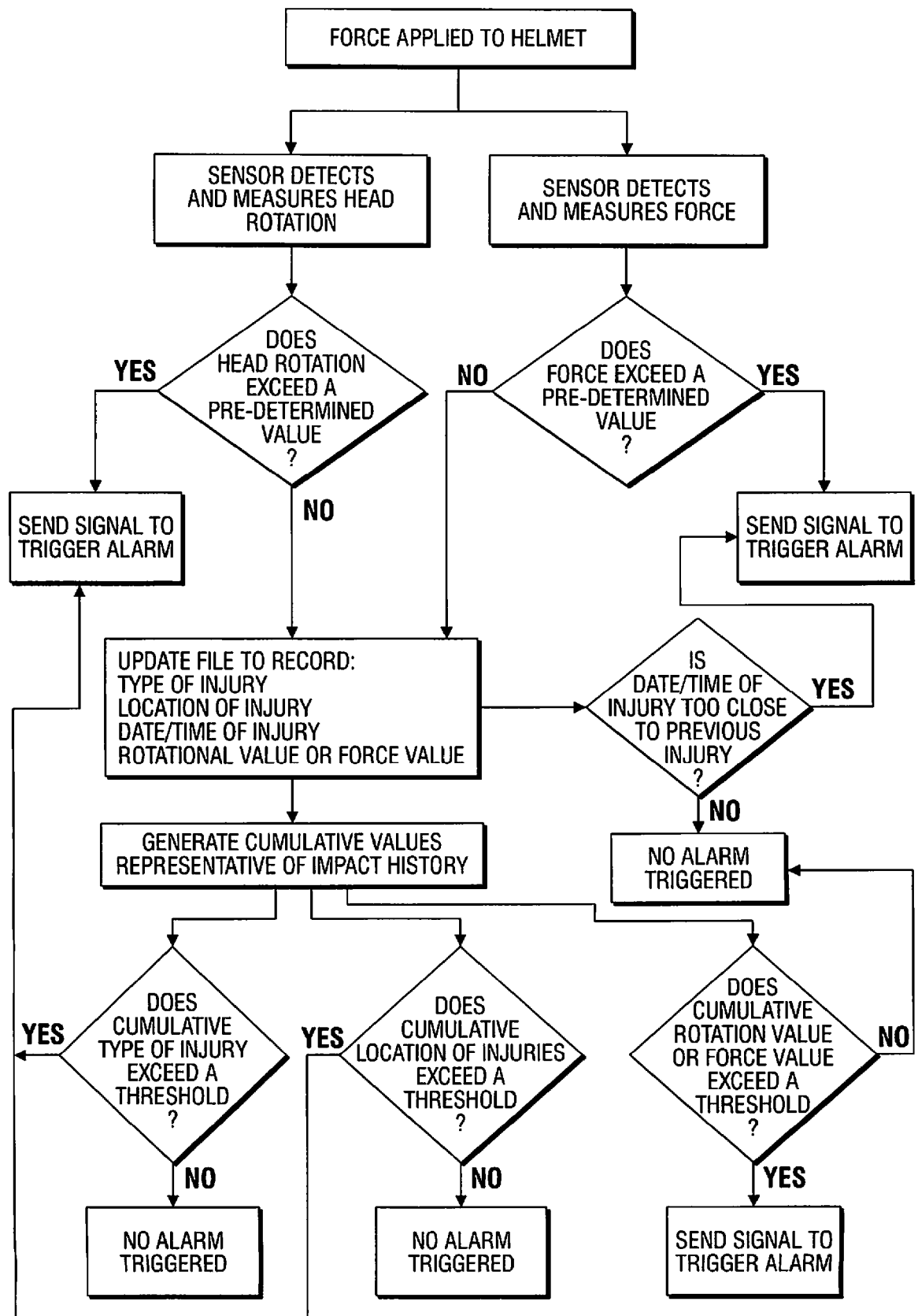
FIG. 12 is a flow chart showing a second embodiment of an impact tracking helmet of the present invention wherein rotational movement and direct impact to the helmet/head is measured and if such measured value exceeds a predetermined value, or cumulative predetermined value, an alarm is triggered.

An alternate embodiment of the helmet and impact tracking system contained therein is depicted in the flow chart of FIG. 12 and schematic block diagram of FIG. 16. The system and method includes an alarm system 124 provided in the helmet so that the wearer and others are alerted to the danger or potential danger of brain injury. In addition, cumulative calculations are performed to compute cumulative effect of impact and injury. The alarm of this system can be triggered by a single impact incident or triggered by a cumulative calculation of one or more measured incidents/impacts.

More specifically, a sensor(s) 112 detects and measures head rotation and/or external force applied to the helmet as in the embodiment of FIG. 11. The measured rotational force R4 is sent via a first signal to the processor 120. The processor 120 receives the signal indicative of the measured rotational force R4 where it is compared to a predetermined or threshold value R3. (Note that R4 can be the same as R2 of FIG. 11 or alternatively another value). The threshold value R3 can be the same or different than R1 of the embodiment of FIG. 11. If the measured rotational force R4 exceeds the threshold value R3, a second signal is sent by the processor 120 to the alarm system 124 to trigger the alarm. The alarm can be of various forms such as audible, e.g. a beeping sound, or visual, e.g., a light or LED can be illuminated in the helmet. Similarly, if the sensor 110 detects an external impact force F4 to the helmet, the sensor 110 measures the force and sends a first signal to the processor 120 indicative of the measured external force F4 where it is compared to a predetermined or threshold value F3. Note that F4 can be the same as F2 of FIG. 11 or alternatively another value. The threshold value F3 can be the same or different than threshold value F1 of the embodiment of FIG. 11. If the measured force F4 exceeds the threshold value F3, a second signal is sent to the alarm system 124 to trigger the alarm.

If the measured rotational force R4 or measured external force F4 does not exceed the predetermined values R3 or F3, respectively, then the data is transferred to the storage file 122 to enable cumulative calculations. The data storage file 122 in the helmet is updated to record one or more, and preferably all, of the following data (parameters): 1) the type of injury; 2) the location of the injury; 3) the date and time of injury; and 4) the force value, and then a cumulative total of each of these parameters is calculated and stored in the file. Once the cumulative value of each of these incidents/ parameters is generated, which is representative of the wearer's personal history of injury incidents, it is compared to a predetermined or threshold value correlating to a safe cumulative value. The processor 120 includes an algorithm to perform these computations and compare them to either individual cumulative values for each parameter or compute a value based on a combination of one or more of the parameters. For example, if the cumulative value of any one of these parameters, e.g., frequency of impact/injury, exceeds a threshold cumulative value of such frequency, then a signal is sent to trigger the alarm. On the other hand, if none of the cumulative values exceed the threshold value, then the alarm is not triggered, but the storage file remains updated with the new data so the values can be recalculated upon receipt of new data in response to subsequent impact to access if an alarm situation is warranted. Note that even if none of the cumulative values exceeds the specific threshold value for that parameter, in some embodiments, the combination of two or more might together compute as an "event" and trigger the alarm. Thus, the processor can evaluate the combination of the parameters (data) in accordance with the algorithm to evaluate whether the combination of two or more of the cumulative values will trigger an "event" thereby activating the alarm system 124.

Also note that the system of FIG. 12 can be configured in alternate embodiments that if the head rotation R4 or impact force F4 exceeds the values R3 and F4, and the alarm system 114 is triggered, these values are transmitted to the storage file 122 and considered in the cumulative calculations generated. This ensures that the forces which trigger the alarm remain part of the impact history. Thus, in this embodiment, the flow chart of FIG. 12 would include an arrow that in addition to sending a signal to trigger an alarm (in response to the first decision box), would also show data being sent to the storage file to update the record.

Note that in certain embodiments of the system of FIG. 12, the predetermined value R3 and F3 are different, i.e., greater, than the first predetermined values R1 and F1 of FIG. 11. That is, in such embodiments, a comparative analysis is first made by the processor 120 to determine if this first (lower) predetermined value R1, F1 is exceeded. If it is exceeded, than a comparison is made to R3 and F3 and the foregoing steps of FIG. 12 apply. However, in such embodiments if the force R4 or F4 does not exceed this lower value R1, F1, it is considered a non-event as in the system steps of FIG. 11, and no data is transferred, thereby ensuring that minor impacts on the helmet which have no adverse bodily effect are not transmitted to the storage file register and are omitted from any injury calculation or evaluation. Note these identical steps to that of FIG. 11 regarding the first predetermined values are omitted from the flow chart of FIG. 12 for clarity. If the force R4 or F4, on the other hand, does exceed the first predetermined value R1 or F1, it constitutes an "event" and is then compared to the predetermined value R3, F3 in accordance with the first decision box of FIG. 12.

Figure 13:
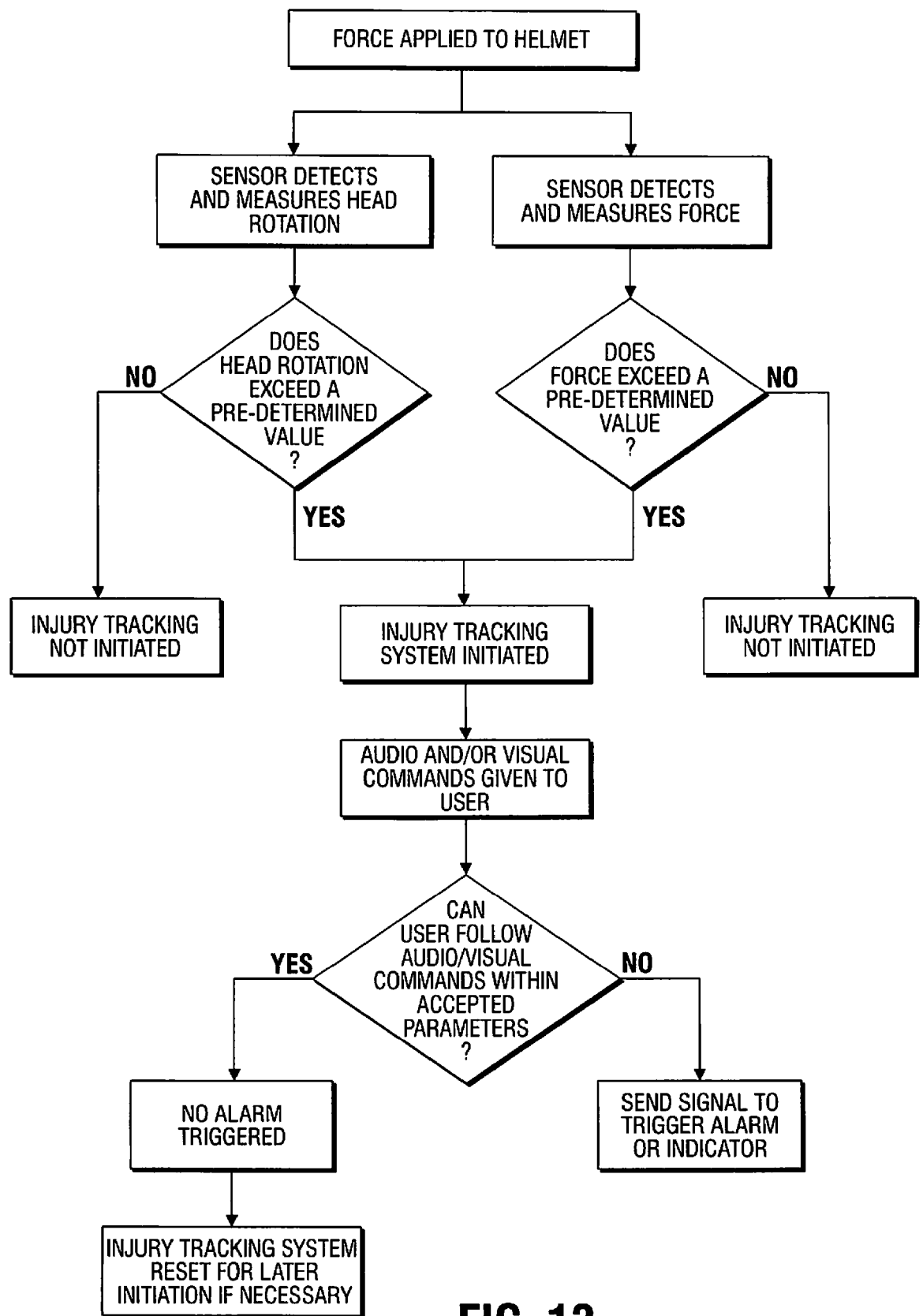
FIG. 13 is a flow chart showing a third embodiment of an impact tracking helmet of the present invention wherein an injury tracking system to assess brain injury is triggered/activated if rotational movement or direct impact exceeds a predetermined value.

The alternate embodiments of FIGS. 13 and 14 provide an injury tracking system where the helmet wearer's injury can be assessed right on site. That is, the helmet contains software to assess brain injury patterns by various methods such as an eye tracking system to assess the focusing/concentration ability of the wearer, a motion tracking system to determine if the user can follow a set of verbal commands to move parts of his body, a hearing testing system to determine the wearer's response to commands, a verbal testing system to determine the wearer's verbal response to questions and/or commands, as well as other forms of testing the wearer, including a smell test emitter of a stimulant gas or liquid. As can be appreciated, such systems can utilize for example, visual, verbal, olfactory and/or auditory testing. If the user fails the injury assessment test by not performing the commands within acceptable preset standards/parameters, then an alarm is triggered to alert the wearer and others that sufficient brain injury, e.g., a concussion, has occurred. Consequently, the helmet itself can function as "on site physician." Note the injury testing in the embodiment of FIG. 14 differs from that of FIG. 13 in that it is also tied into the accumulation of incidents of injury, severity and frequency, as explained in detail below.

Turning first to the embodiment of FIG. 13, as in the embodiment of FIG. 11, one or more sensors detects and measures head rotation and/or external force applied to the helmet. The measured rotational force is sent by the sensor 134 (FIG. 17) to a processor 130. The processor 130 receives the signal from the sensor 134 indicative of the measured rotational force R6 where it is compared to a predetermined or threshold value R5. If the measured rotational force R6 does not exceed a threshold value R5, then it is considered a "non-event" and the injury tracking system 138 is not initiated. Similarly, if the measured external force F6 received from force sensor 132 by processor 130 does not exceed a threshold value F5, then it is considered a "non-event" and the injury tracking system 138 is not initiated. Note the values R6 and F6 can be the same as R4 and F4 of the embodiment of FIG. 12 or alternatively other values. Additionally, the threshold values R5 and F5 can be the same or different than values R3 and F3 of FIG. 12.

Figure 17A:
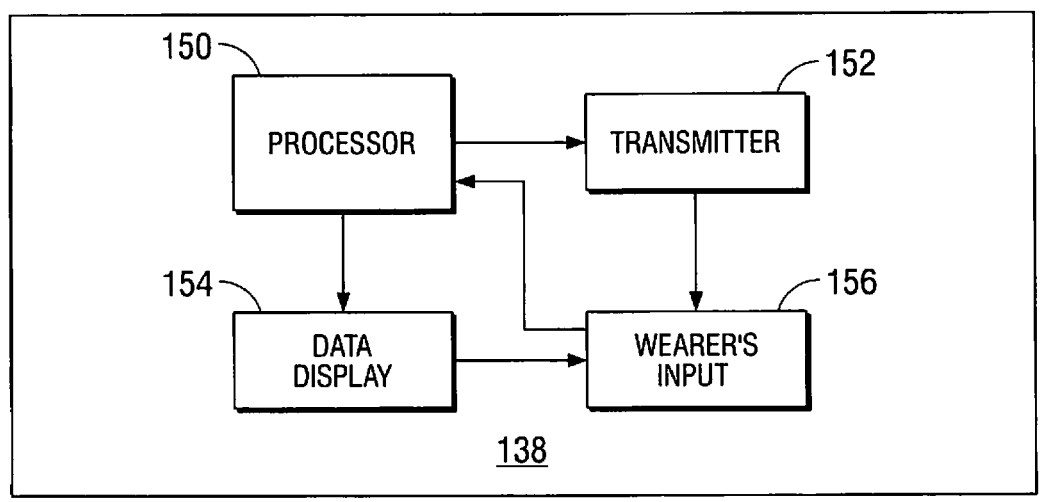
FIG. 17A is a schematic block diagram showing the impact tracking system of FIGS. 13 and 17.

On the other hand, if the measured rotational force R6 or the measured external force F6 exceeds the predetermined or threshold value R5, F5, respectively, a signal is sent to the injury tracking system 138 to initiate (activate) the system. The injury tracking system 138 is show schematically in the block diagram of FIG. 17A. The system 138 includes a processor 150 and a transmitter 152 to transmit commands to the wearer. The wearer responds (input 156) to the commands and the responses are inputted to the processor 150 for assessment. A data display 154 could also be provided which provides visual commands or prompts (instructions) to the wearer whose responses are inputted to the processor 150.

More specifically, when the injury tracking system 138 is initiated (activated), the command or prompt is given to the wearer (user) such as a visual command for the user to move his hand or foot, or the user is instructed to focus his vision on various screens, such as display screen 154. If the wearer can follow the commands and satisfy the testing parameters, no alarm is triggered and the injury tracking system 138 is reset for later initiation if necessary. However, if the user cannot follow the commands within the acceptable parameters, a signal is sent to the alarm system 140 to trigger the alarm or other indicator. The alarm can be of various forms such as audible or visual, e.g., a beeping sound can be heard or a light or LED can be illuminated in the helmet.

A storage file 136 could also be provided to record the type of injury, location of injury, date/time of injury and force value in the same manner as the system of FIG. 11.

In the alternate system of FIG. 14A, 14B (contained on two sheets of drawings-FIGS. 14A-14B due to the length of the flow chart), the injury tracking system is initiated either by a) initial measured force impact (as in the system of FIG. 13) or b) by cumulative calculations of specified parameters. That is, viewed in one way, the system of FIG. 14A, 14B differs from that of FIG. 13 in that it also calculates cumulative history as in the system of FIG. 12, and uses these calculations to activate the injury tracking system, if necessary, not just relying on the initial measurements as in the system of FIG. 13. Viewed in another way, this embodiment of FIG. 14A, 14B differs from that of FIG. 12 in that the cumulative calculations alone are not sufficient to trigger the alarm, but instead, a test of the wearer's motor skills, focus, hearing, etc. is utilized to detect the severity of the injury, and only if the wearer's responses to the testing are determined deficient, is the alarm triggered. This provides on site assessment of injuries and can avoid premature initiation of an alarm since the trigger is not based solely on cumulative history but on a measurement of the wearer's functional abilities which are representative of the severity of the injury.

More specifically, as in the previous embodiments, in the alternate system and method of FIG. 14A, 14B, a sensor detects and measures head rotation and/or external force applied to the helmet. The measured rotational force is compared to a first predetermined or threshold value. If the measured rotational force sent to the processor from the sensor (such as rotation sensor 134 of FIG. 17) does not exceed a threshold value, a signal is not sent from the processor to the injury tracking system (such as injury tracking system 138 of FIG. 17) and the injury tracking system is not initiated to activate a test for the wearer as it is computed as a "non-event." However, the data, e.g., type of injury, location of injury, date/time of injury, force value, etc., is sent to the storage file to update the register to record the data (parameters) in the same manner as in the system of FIG. 12. Similarly, the measured external force measured by a sensor (such as force sensor 132 of FIG. 17) is compared by a processor to a predetermined or threshold value. If the measured force does not exceed a threshold value, a signal is not sent by the processor to the injury tracking system (such as injury tracking system 138) and the injury tracking system is not initiated to activate the test for the wearer as it is computed as a non-event. However, the data, e.g., type of injury, location of injury, date/time of injury, force value, etc., is sent to the storage file to update the register to record the data (parameters) in the same manner as in FIG. 12. Thus, if the measured rotational or impact force does not exceed the predetermined values, then the data is transferred to the storage file to perform cumulative calculations of the type of injury, location of injury, date/time of injury and the rotational or impact force value in the same manner as described above in conjunction with the embodiment of FIG. 12. Once a cumulative total of each of these parameters is calculated, a cumulative value of each of these parameters is generated, which is representative of the wearer's personal history of injury incidents, and it is compared to a predetermined or threshold value correlating to a safe cumulative value in accordance with an algorithm which evaluates the cumulative values for each parameter as well as a combination of cumulative values to determine if the combination presents a significant injury as described above in the system of FIG. 12. If the threshold value representative of the safe cumulative value, or combination value is exceeded, then a signal is sent to initiate the injury tracking system, and the system runs as in the embodiment of FIG. 13 and FIG. 17 described above, triggering an alarm or indicator if the wearer does not pass the test, i.e., does not satisfy the prompts or commands transmitted to the wearer, which is indicative of sufficient brain injury. If the cumulative values or combination values does not exceed the threshold value, then the injury tracking system is not triggered but the storage file remains updated with the new data for later addition to subsequent force impacts so the values can be recalculated to assess if activation of the tracking system is warranted at a later date.

In other words, in the system of FIG. 14A, 14B, cumulative values are computed and compared to the threshold values in the same manner as FIG. 12, except that if the threshold is exceeded, instead of triggering an alarm as the next step as in FIG. 12, the injury tracking system 138 is activated to determine if an alarm needs to be triggered. The injury tracking system can be the same as described above with respect to FIG. 13 and for brevity is not repeated herein. Note that the provision of an algorithm to calculate the cumulative values, and evaluate their significance either independently or as a combination can be the same as that described above with respect to FIG. 12 and therefore for brevity is not repeated herein.

If, on the other hand, the measured rotational force from the sensor (e.g., sensor 132) exceeds a threshold or predetermined value (see first decision box of FIG. 14A), a signal is sent from the processor to the injury tracking system to activate the test for the wearer as described above in conjunction with FIG. 13. Similarly, if the measured force from the sensor (e.g., sensor 134) exceeds a threshold or predetermined value (FIG. 14A), a signal is sent from the processor to the injury tracking system to activate the test for the wearer. The tracking system tests the wearer's motion, force/concentration, hearing, etc. in the manner described above to determine if it conforms to acceptable parameters, and if not, an alarm is triggered or other indicator is activated to alert the wearer and others that sufficient injury has occurred.

If measured force exceeds the threshold value to trigger the injury tracking system, preferably data (e.g., type, location, and date of injury and force value) is sent to the storage file to record the history for later retrieval from memory and evaluation.

The foregoing helmets thus contain the wearer's information/history which is easily accessible from memory. The tracking system can advantageously replace the on field physician. The tracking system can be placed for example on Plexiglas face protector on the helmet or integrated into google type glasses on the front of the helmet. FIG. 18 illustrates an example where the tracking system is placed on the face protector of the helmet.

The force sensors/transducers can be placed at various regions of the helmet so as to monitor impact at any portion of the helmet.

In addition to providing systems as outlined in the flow charts of FIGS. 11-14B, the present invention can also include methods for tracking impact on a helmet comprising the steps set forth in the flow charts of FIGS. 11-14B.

Note the processor can be implemented utilizing a microprocessor, micro-computer, central processing unit or any other device that manipulates analog and/or digital signals. The memory module, e.g., storage file, performs a storage function while the processor executes operational instructions. The systems disclosed herein can be wireless.

There are various ways to power the helmets disclosed herein such as pressure, battery, polar, solar kinetic energy, etc.

The foregoing helmets can also include one or more cameras so that the wearer's reaction can be viewed during activation of the injury tracking system. Cameras can be aligned with the wearer to view what the wearer is visualizing, aligned with the wearer's eyes and/or additional cameras viewing from behind the wearer or to either side of the wearer.

As noted above, the helmets with impact tracking and/or injury tracking systems of FIGS. 11-18 can also optionally include structure to vary shock absorption and/or to diffuse and disperse the impact as in the helmets of FIGS. 1-10. For example, in one embodiment, a plurality of air cells with relief valves are positioned within the helmet as described above. The cells can be of different characteristics so their shock absorption function is initiated depending on the extent of impact. The shock absorbers can alternatively be composed of compressible foam with differing flexibility/compressibility as described above. The outer shell can also optionally include a low friction surface to reduce the force impact by diffusing the force of a direct hit to the helmet. The outer shell can also optionally spin with respect to the outer body. Thus, the helmets of FIGS. 1-10 with varying shock absorption can optionally be provided with any of the systems of FIGS. 11-18.

Helmets for various sports and activities are contemplated, such as, without limitation, football, hockey, lacrosse, bicycle, motorcycle, etc. as shown for example in FIGS. 10A, 10B, 10C.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A helmet for tracking impact comprising:
   a) at least one sensor within the helmet;
   b) a built in injury tracking system;
   c) a processor in communication with the at least one sensor;
   d) a storage file in communication with the processor; and
   e) a register updated by the storage file to record cumulative data including:
      i) a type of injury;
      ii) an exact location of injury;
      iii) a date and time of injury; and
      iv) a force value of a force applied to a head of a wearer of the helmet, wherein,
   the at least one sensor measures a force applied to the helmet and sends a signal indicative of the measured force to the processor, the processor receiving the signal indicative of the measured force and comparing the measured force to a predetermined value;
   if the measured force exceeds the predetermined value, first data of the measured force is sent to the storage file to record the measured force and store the measured force within the helmet;
   if the measured force does not exceed the predetermined value, second data of that measured force is sent from the processor to the storage file to record the measured force and store the measured force within the helmet, and the processor calculates cumulative impact data based on the second data below the predetermined value and updates the storage file to include the cumulative impact data to assess if activation of the tracking system is warranted; and
   the built in injury tracking system is activated if the cumulative impact data exceeds a threshold, the injury tracking system requiring the wearer of the helmet to perform a set of commands within acceptable preset parameters, the built in tracking system including one or more of an eye tracking system, a motion tracking system, a hearing testing system, or a verbal testing system to determine a verbal response of the wearer to multiple questions or commands.

2. The helmet of claim 1 wherein the measured force is a rotational force applied to the head of the wearer of the helmet and the first and second data include a force value of the measured force.

3. The helmet of claim 1, wherein the measured force is an impact force applied to the head of the wearer of the helmet and the first and second data include a force value of the measured force.

4. The helmet of claim 1, further comprising a plurality of shock absorbers including at least one first shock absorber having a first shock absorption characteristic and at least one second shock absorber having a second shock absorption characteristic, the second shock absorption characteristic being different than the first shock absorption characteristic, wherein the first shock absorption characteristic provides a lower activation threshold than the second shock absorption characteristic such that activation of the first and second sets of shock absorbers is dependent on the force applied to the helmet.

5. The helmet of claim 1, wherein the storage file updates the register and the first and second data are stored in the register and wherein the register is repeatedly updated as additional data is received in response to subsequent measured forces detected which exceed the predetermined value and which are below the predetermined value, the first and second data being retrievable for evaluation.

6. The helmet of claim 1, wherein if the wearer does not perform the set of commands within the acceptable preset parameters, a signal is sent to an alarm system to trigger an alarm.

7. A helmet for tracking impact comprising:
   a) an alarm system in the helmet;
   b) a built in injury tracking system;
   c) at least one sensor;
   d) a processor in communication with the at least one sensor;
   e) a storage file in communication with the processor;
   f) a register updated by the storage file to record cumulative data including:
      i) a type of injury;
      ii) an exact location of injury;
      iii) a date and time of injury; and
      iv) a force value of a force applied to a head of a wearer of the helmet; and
   g) a built in injury tracking system, wherein,
   the at least one sensor measures a force applied to the helmet and sends a signal indicative of the measured force to the processor;
   the processor receives the signal indicative of the measured force and compares the measured force to a predetermined value;
   if the measured force exceeds the predetermined value first data is sent to the storage file to record the measured force and store the measured force within the helmet;
   if the measured force does not exceed the predetermined value, second data of that measured force is sent from the processor to the storage file, and the processor calculates cumulative impact data based on the second data and updates the storage file to include the cumulative impact data to assess if activation of the built in injury tracking system is warranted; and
   the built in injury tracking system is activated if the cumulative impact data exceeds a threshold, the injury tracking system requiring the wearer of the helmet to perform a set of commands within acceptable preset parameters, the built in tracking system including one or more of an eye tracking system, a motion tracking system, a hearing testing system, or a verbal testing system to determine a verbal response of the wearer to multiple questions or commands.

8. The helmet of claim 7, further comprising an outer shell having an inner surface and an outer surface and a plurality of shock absorbers, the shock absorbers being positioned internal of the outer shell, the plurality of shock absorbers including at least one first shock absorber having a first shock absorption characteristic and at least one second shock absorber having a second shock absorption characteristic, the second shock absorption characteristic being different than the first shock absorption characteristic, wherein the first shock absorption characteristic provides a lower activation threshold than the second shock absorption characteristic such that activation of the first and second sets of shock absorbers is dependent on the force applied to the helmet.

9. The helmet of claim 7, wherein the built in injury tracking system includes a transmitter to transmit commands to the wearer of the helmet and responses of the wearer are inputted to and evaluated by the processor.

10. The helmet of claim 9, wherein if the wearer does not perform the set of commands within the acceptable preset parameters, a signal is sent by the processor to the alarm system to trigger an alarm and if the wearer does perform the set of commands within the acceptable preset parameters, the signal for triggering the alarm is not sent to the alarm system.

* * * * *